(12) United States Patent
Attie et al.

(10) Patent No.: US 7,442,500 B2
(45) Date of Patent: Oct. 28, 2008

(54) METHODS OF DIAGNOSING SUSCEPTIBILITY TO OBESITY

(75) Inventors: Alan D Attie, Madison, WI (US); Samuel T Nadler, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/955,367

(22) Filed: Sep. 18, 2001

(65) Prior Publication Data

US 2003/0013093 A1    Jan. 16, 2003

Related U.S. Application Data

(60) Provisional application No. 60/233,339, filed on Sep. 18, 2000.

(51) Int. Cl.
*C12Q 1/68* (2006.01)
*C07H 21/04* (2006.01)

(52) U.S. Cl. .................. 435/6; 536/23.2; 536/23.5

(58) Field of Classification Search ............ 435/6, 435/287.2; 536/23.2, 23.5
See application file for complete search history.

(56) References Cited

OTHER PUBLICATIONS

Andreelli, F. et al. Defective regulation of phosphatidylinositol-3-kinase gene expression in skeletal muscle and adipose tissue of non-insulin-dependent diabetes mellitus patients. Diabetologia 42:358-364 (Mar. 1999).*
Choo,H.J., et al., "Mitochondria are impaired in the adipocytes of type 2 diabetic mice," Diabetologia 48:784-791 (2006).
Ducluzeau, P-H., et al., "Regulation by Insulin of Gene Expression in Human Skeletal Muscle and Adipose Tissue," Diabetes 50:1134-1142 (2001).
Sewter, C., et al., "Human Obesity and Type 2 Diabetes are Associated with Alterations in SREBP1 Isoform Expression That are Reproduced . . . ," Diabetes 51:1035-1041 (2002).
Shimomura, I., et al., "Nuclear Sterol Regulatory Element-binding Proteins Activate Genes Responsible for the Entire . . . ," J. Biol. Chem. 273:35299-35306 (1998)(abstract).
Yang, X., et al., "Evidence of Impaired Adipogenesis in Insulin Resistance," Biochem Biophys Res Commun 14:317(4):1045-51 (2004)(abstract).
Yki-Jarvinen, H., "Role of insulin resistance in the pathogenesis of NIDDM," Diabetologia 38:1378-88 (1995)(abstract).
Asmann, Y.W., et al., "Skeletal Muscle Mitochondrial Functions, Mitochondrial DNA Copy Numbers, and Gene Transcript Profiles . . . ," Diabetes 55:3309-3319 (2006).
Lee, Y.H., et al., "Microarray profiling of isolated abdominal subcutaneous adipocytes from obese vs non-obese Pima Indians . . . ," Diabetologia 48:1776-1783 (2005).
Clee, S.M., et al., "Positional cloning of Sorcs1, a type 2 diabetes quantitative trait locus," Nature Genetics 38:688-693 (2006).
Clee, S.M., et al., "The Genetic Landscape of Type 2 Diabetes in Mice," Endocrine Reviews 28:48-83 (2007).
Goodarzi, M.O., et al., "SORCS1: A Novel Human Type 2 Diabetes Susceptibility Gene Suggested by the Mouse," Diabetes 56:1922-1929 (2007).
Lee, Y.H., et al., (2005) Electronic supplementary material is available in the online version of this article at http://dx.doi.org/10.1007/s00125-005-1867-3.
Montague, C.T., et al., "Congenital leptin deficiency is associated with severe early-onset obesity in humans," Nature 387:903-908 (1997).
Stoehr, J.P., et al., "Genetic Obesity Unmasks Nonlinear Interactions Between Murine Type 2 Diabetes Susceptibility Loci," Diabetes 49:1946-1954 (2000).
Zhang, Y., "Positional cloning of the mouse obese gene and its human homologue," Nature 372:425-432 (1994).

* cited by examiner

*Primary Examiner*—Diana B Johannsen
(74) *Attorney, Agent, or Firm*—Quarles & Brady LLP

(57) ABSTRACT

A gene expression pattern analysis has identified genes the expression patterns of which are different in adipose cells of individuals who have Type 2 Diabetes Mellitus from the cells of individuals who do not have the disease. This information provides a mechanism for the genetic diagnosis of the disease.

5 Claims, No Drawings

METHODS OF DIAGNOSING SUSCEPTIBILITY TO OBESITY

CROSS-REFERENCE TO RELATED APPLICATIONS

This application claims priority from provisional patent application Ser. No. 60/233,339 filed Sep. 18, 2000.

STATEMENT REGARDING FEDERALLY SPONSORED RESEARCH OR DEVELOPMENT

This invention was made with United States government support awarded by the following agency: NIH HL56593. The United States has certain rights in this invention.

BACKGROUND OF THE INVENTION

DNA microarrays are small dense arrays of DNA probes arranged on a substrate. The probes on the microarrays are arranged in cells, each of which contains only DNA probes derived from a single DNA sequence. When the DNA microarray is exposed to test mRNA of unknown or mixed sequence, the test nucleotides will hybridize or bind to the probes in one of more cells of the array. The test nucleotides will only bind to those probes the sequence of which is complementary to a DNA on the array. By intelligently constructing such DNA microarrays, it now is possible to construct microarrays which can be used to explore the expression patterns of human or animal genes during any number of physiological processes. For example, if a scientist had available a microarray including the complete set of the genes expressed by an organism, the scientist could then test against that array the mRNA produced in cells of various tissues of the organism during development. This would enable the scientist to determine which genes turn on and off when during the development of that tissue of the organism. Similar studies can be imagined to study disease susceptibility or progression.

Obesity is a strong risk factor for the development of Type 2 Diabetes Mellitus, a disease characterized by insulin resistance, relative insulin hyposecretion, and hyperglycemia. In fact, over 80% of individuals with Type 2 Diabetes Mellitus are obese. However, only 10% of individuals who are obese are diabetic. It is still unclear what determines which obese, non-diabetic individuals will transition to diabetes.

In the course of transition from healthy to diabetic, it is common for obese individuals to become insulin resistant. The concept of insulin resistance is that the body becomes less sensitive, or even entirely insensitive, to insulin levels in the blood, and hence the metabolic activities triggered by insulin in normal individuals do not proceed or proceed at lower levels. As a result of that lowered metabolic response, the normal physiological feedback mechanisms cause the pancreas to increase insulin production to compensate for the insensitivity of the response to insulin. As the insulin response continues to decrease, insulin production continues to increase until, it is thought, the insulin producing cells are simply exhausted. Thus the onset of resistance to insulin may serve as a predictor of eventual diabetic disease in an individual.

The Obese mouse model represents a well-studied and accepted animal model for human obesity. These animals are homozygous for a gene, designated ob, which is a nonsense mutant form of the gene encoding leptin, a satiety factor secreted by adipocytes. The ob animals are markedly hyperphagic. However, despite extreme obesity, C57BL/6J (B6) ob/ob mice have only mild transient hyperglycemia. The ob mutation can be introgressed into the BTBR mouse strain to obtain severely diabetic mice. Together, these animals provide a functional animal model for the study of obesity present with or without diabetes.

BRIEF SUMMARY OF THE INVENTION

The present invention is summarized in that the first evaluation of the genetic basis for diabetic disease has now been made. The expression patterns of several genes have been characterized in change in individuals from healthy to diabetic. This makes possible the first genetic evaluations of individuals to determine susceptibility to type 2 diabetes.

The present invention also enables the design of genetic based tests for predicting and detecting the onset of insulin resistance based diabetes. This genetic analysis has revealed changes in gene regulation in adipocytes associated with the onset of this disease, this making it possible to assay for the gene regulation pattern in adipocytes in obese individuals to test for possible diabetic condition.

Other objects, advantages and features of the present invention will become apparent from the following specification.

BRIEF DESCRIPTION OF THE SEVERAL VIEWS OF THE DRAWINGS

None.

DETAILED DESCRIPTION OF THE INVENTION

While obesity is strongly correlated with Type 2 Diabetes, the role of obesity and genetics in the onset of this disease are not well understood. Here, for first time, the genes which have expression patterns diagnostic of the onset of diabetes are identified. This development makes possible the early diagnosis of the disease and early intervention so that the disease can be more successfully managed. In addition, also disclosed here are the genes the expression patterns of which change during the development of insulin resistance. Since the development of insulin resistance is a possible precursor to the development of diabetes, the identification of these gene expression patterns also provide diagnostic tools to identify or treat individuals at risk of developing diabetes.

This work made use of DNA microarrays to determine gene expression patterns in adipose tissue of obese individuals and in individuals having diabetes, using the mouse animal model. We used the DNA microarrays to identify changes in gene expression in both obesity and Type 2 Diabetes Mellitus. By using different strains of mice, we were able to identify those genes whose expression changed at onset of diabetes, independently of strain background. The identified genes are therefore most likely to be relevant in obesity and diabetes independent of other genetic background. Of the over 11,000 genes examined, over 200 genes showed consistent changes with obesity. Then because insulin resistance is a characteristic of the disease, we performed a similar study on mice that showed evidence of insulin resistance. In this study, we compared gene expression patterns in insulin resistant adipose tissue as compared to insulin sensitive adipose tissue. The insulin sensitivity was assessed by measuring the rate of glucose transport in response to insulin in freshly isolated adipocytes.

We were also able to identify a large number of genes whose level of gene expression in adipose tissue strongly correlated with the progression from normoglycemic obesity to obesity concomitant with diabetes. Of the genes that were evaluated by our analysis, the expression of some changed with obesity alone, while the expression of others was identified as important in diabetes alone. A smaller subset of these genes, including the b-3 adrenergic receptor, demonstrated changes in expression in both diabetes and obesity.

This data shows that many of the changes in gene expression in diabetic adipocytes are a reversal of the pattern of gene expression which is characteristic of adipocyte differentiation. To facilitate that comparison, the genes in the tables below are organized in a manner similar to the patterns observed during the process of adipocyte differentiation. Cornelius et al., *Ann. Rev. Nutr.* 14, 99-129 (1994), organized the changes in gene expression observed in adipogenesis into five groups: hormone signaling and action, lipogenesis and lipolysis, cytoskeletal and extracellular, secreted, and proteins of unknown function. In this study, we observed changes in mRNA levels of 18 of those genes, distributed across four of the five classes. The expression levels of all but one of the genes changed in the opposite direction from the changes observed during adipocyte differentiation.

Tables 1, 2, and 3 attached to this specification summarize the results of this analysis. Table 1 lists the genes for which decrease levels of gene expression was found with increasing obesity in each mouse strain. The fold changes indicated in the tables are approximate, as the level of gene expression may have been outside the linear ranges of detection in one of the comparisons. Genes listed as □similar to□ are ones which show sequence similarity with $e<5\times10^{-5}$, Altsuch et al., *J. Mol. Biol.* 215, 403-410 (1990). Table 2 shows the list of genes the expression of which increase with increased obesity. Table 3 lists the changes in gene expression that correlated with the development of hyperglycemia. The R-values in Table 3 are calculated using the rank order of the five sets of animals with increasing hyperglycemia. Here fold changes represented by □n/a□ means that the mRNA level increased from, or decreased to, an expression level outside the linear range of detection.

In the tables, the genes are organized into groups, similar to the groupings of gene expression patterns as previously identified during the differentiation of adipocytes. In Table 1, there are groups of genes associated with hormones and signal transduction, mitochondrial function, lipid metabolism, transcription factor, secreted proteins, and others. In Table 2, the genes are grouped as cytoskeletal and ECM, lysosomal, immune/complement genes, cell proliferation genes, adipose-specific genes, membrane proteins and others. In Table 3, the gene groupings are signal transduction, secreted proteins, protein synthesis and processing, cytoskeletal and ECM, transcription factors, others and metabolism genes.

One strategy to design a diagnostic test for the initiation of progression to insulin resistance or diabetes would be to assay for changes in the level of expression of any of the genes in Tables 1, 2 or 3. Any of these genes could be combined with assays for the level of expression of any others to test for this progression. An assay testing the expression level of a larger number of genes would add to the confidence in the result, but testing all of the genes on the tables would not be necessary or appropriate.

In one useful strategy for the construction of a panel or array to test for progression to insulin insensitivity or to diabetes, one would select a representative gene from each of four different gene groupings as listed either or both of Table 1 or 2. The assay would then test for the associated increase or decrease in gene activity associated with the progression. For example, an assay might look at the expression level of one lipid metabolism gene from Table 1, one transcription factor gene from Table 1, one signal transduction gene from Table 2, and one secreted protein from Table 2. Of course, one would look for decreases in gene expression in the gene selected from Table 1 and increases in gene expression for the genes selected from Table 2. The selection of genes from four different groupings adds to the reliability of the assay by demonstrating that differing cellular functions are demonstrating the effect. For an assay of increased stringency, genes from six or either different gene groupings could be used.

One particularly significant gene which is a candidate for inclusion in any such assay is SREBP (Table 1). This gene encodes a protein transcription factor, which means that the expression of this gene triggers activation of a series of additional genes in the adipose cell. Thus changes in the level of expression of this gene are magnified in effect. An assay for the level of expression of this gene may be the most significant of the genes listed in the tables, and a sensitivity to any decrease in the level of expression of this gene is an observation that should be accorded significance. The data indicates that the level of expression of SREBP is a good predictor of susceptibility to diabetic disease.

In all three tables, the genes from the mouse insulin model are identified by reference to GenBank™ accession numbers. In each table as well, the homologous human gene is also listed by reference to GenBank™ accession numbers. The human gene are exemplary, and other homologs may be used as well. Obviously, in an assay intended to diagnose human disease, the human genes should be used. All the respective gene sequences can be retrieved in their entirety from the GenBank™ depository on-line with these accession numbers, as is well known to those of skill in this art.

Changes in gene expression in adipose tissue alone might or might not be sufficient to cause diabetes. Alterations in muscle, liver and pancreatic b-cells are probably also required. However, recent studies in mice that lack white adipose tissue show that adipocytes play an important role in the development of diabetes. For example, transgenic mice lacking adipose tissue due to disruption of transcriptional regulation by C/EBPs and Jun, develop hyperglycemia and hyperinsulinemia, two hallmarks of type 2 diabetes. Similarly, adipocyte-specific overexpression of a constitutively active form of SREBP leads to dramatic loss of white adipose tissue and subsequent development of diabetes in mice. It is currently believed that a change in lipogenic capability in adipose tissues is certainly indicative of a change to insulin resistance and may be a causative agent for the development of diabetic disease.

The changes in gene expression that we observed are provocative in that the onset of diabetes in our model system correlated with alterations in the expression of many mRNAs coding for signal transduction proteins that have been previously implicated in diabetes. For example, Fyn mRNA levels increased with hyperglycemia. Fyn has recently been implicated in the compartmentalization of insulin signaling through its interaction with c-Cb1. Similarly, we observed an increase in mRNA for Flk-2, a tyrosine kinase that promotes hematopoiesis through interactions with Grb2 and Shc, two important mediators of insulin signaling.

The expression of many transcription factors correlated with diabetes. Expression of BF-2 and int-1 both increased with diabetes. BF-2 has been described in the context of neuronal development and belongs to the same family as HNF3, an important adipogenic transcription factor. Int-1 is a proto-oncogene involved in the proliferation of mammary tumors. A decrease in mRNA levels was observed for the transcription factors Dishevelled-3 (Dvl-3), Dlx5, and Pale Ear (ep). No association between hyperglycemia and Dishevelled-2 or Dlx5 has been previously reported. The potential role of Pale Ear in diabetes progression is intriguing. Mutations in the orthologous human gene cause Hermansky-Pudlak syndrome in humans, a rare disorder associated with impaired vesicular transport, a critical process in insulin-stimulated glucose uptake.

The mRNA levels of another protein implicated in vesicular transport, tctex-1, decreased with diabetes. Tctex-1 comprises one of the three light chains in cytoplasmic dynein. It plays an important role in many aspects of membrane and vesicular transport. Impaired ability of cells to translocate glucose transporter-containing vesicles to the plasma membrane in response to insulin would result in insulin resistance, an important contributor to the development of Type 2 Diabetes Mellitus.

The work described here uses an 11,000 gene murine microarray. Since the total number of genes in the murine genome is currently unknown, but is probably in the range of 50,000 to 150,000 genes, these 11,000 genes represent a sample of perhaps 5-20% of the genome, although they probably contain a higher percentage of genes expressed in adipose tissues. The microarray, commercially available from Affymetrix, Inc., is known as the murine 11k array.

The data presented in this specification can be used both for the study of the onset of diabetic disease as well as providing a tool for developing diagnostic tests for the disease. The genes listed in Table 3 represent the changes to the molecular genetics of the adipose cell which are responsible for the evolution of the cells to a state of diabetic disease. By continuing to correlate this information to the actual occurrence of disease, it will become possible to determine which among the expression patterns of these genes are actually definitive for the onset of diabetic disease. Then that information can be used as a definitive test for the disease. In addition, one can readily envision a diagnostic test, consisting for example of a microarray containing probes for each of the genes in the tables, by which the expression patterns of those genes can be measured in an individual to determine whether that individual has diabetes or has the genetic predisposition to develop diabetes.

It is also envisioned that the information presented here will be valuable to design techniques for intervention in the progression of diabetes disease. Many genes are shown here to be either up-regulated or down-regulated in adipose cells as an individual first becomes insulin resistant and then diabetic. Given the techniques of gene therapy now available to use this information to design intervention strategies to counteract that gene expression pattern. The idea is that one would up-regulate genes which would otherwise be in the process of down-regulation and down-regulate genes which were over-expressing. It is possible to up-regulate genes in mammals by adding additional copies of the genes to cells by gene therapy or by triggering up-regulation of genes by introducing known inducing substances into the individual. For down-regulation, one could introduce an anti-sense genetic construction into the individual or one could use a drug which is known to have a down-regulating effect on the targeted gene. This data thus provides an intervention mechanism through which it is possible to prevent the progression into diabetic disease.

While the data presented here was gathered in a murine animal model, the data should be largely useful as well in humans, using the human homologous genes. Of course, for a human test the genes which would be assayed would be the human analogous of the listed murine genes, but the availability of the entire human genomic sequence makes this analysis both possible and practical.

EXAMPLES

Animals. BTBR, B6 and B6-ob/+ mice were purchased from the Jackson Laboratory (Bar Harbor, Me.) and bred at the University of Wisconsin Animal Care Facility. Mice were housed on a 12 hour light-dark cycle and had ad libitum access to regular chow (Purina #5008) and water. All protocols were approved by the University of Wisconsin—Madison Institutional Animal Care and Use Committee.

Sample Preparation. Epididymal fat pads were isolated from 14-week old mice after a 4-hour fast, and snap frozen in liquid nitrogen. Total RNA was isolated using TriReagent (Molecular Research Center, Inc., Cincinnati, Ohio). cDNA was prepared from equal amounts of total RNA pooled from at least 4 animals using Superscript Choice System™ (GibcoBRL, Grand Island, N.Y.) with a primer containing oligo-(dT) and T7 RNA polymerase promoter sequences. Biotinylated cRNA was synthesized from purified cDNA using the Bioarray High Yield RNA Transcript Labeling Kit™ (Enzo, Farmingdale, N.Y.). cRNA was purified using Rneasy™ columns (Qiagen, Valencia, Calif.), and quantified thereby.

Microarrays. Samples for DNA microarray hybridization were prepared as described by Lockhart et al., *Nat Biotech.* 14, 1675-1680 (1996). Hybridization to Murine 11K arrays was performed for 16 hours at 45° C. Microarrays were washed according to Affymetrix protocols and immediately scanned on a Hewlett-Packard GeneArray® Scanner.

Data analysis. All data sets were normalized to total fluorescence, which represents the total amount of cRNA hybridized to a microarray. The threshold for determining the significance of a change in the level of gene expression was made using an algorithm that requires both a significant absolute and fold change. Identification of genes associated with obesity was determined by selecting only those genes that significantly increased or decreased in every comparison.

Gene expression levels that changed with diabetes were identified by linear regression performed on five groups of animals with increasing hyperglycemia. The correlation between expression levels and rank order of the five groups of animals was determined. This method was preferred to several clustering methods as it focuses specifically on linear trends. Similar genes were observed to change when regressions were performed with average fasting glucose levels of the group of animals instead of the rank order. Genes that correlated with R>0.95 or R<−0.95 and had at least 3 absolute expression levels within the limits of detection were selected.

The strains of lean mice, C57BL/6J, BTBR, and BTBR× B6 F1 (BtB6 $F_1$), all have normal fasting glucose levels. The ob allele causes extreme obesity, but only mild, transient hyperglycemia in the B6 background, (fasting plasma glucose 210±30.7 mg/dl) as separately described (Stoehr, et al., submitted). In contrast, introgression of ob into BTBR animals caused both obesity and severe diabetes with fasting plasma glucose levels of 549±24.5 mg/dl. Obese animals derived from a cross between BTBR and B6 ($F_2$ ob/ob) showed a large range of fasting glucose levels (150-750 mg/dl). Therefore, this $F_2$ population was a means of obtaining obese mice exhibiting different degrees of diabetes.

Gene Expression in Lean and Obese Mice. The gene expression profile of adipose tissue from lean and obese animals in several mouse strains were compared. We assessed the mRNA levels of >11,000 genes. About 10% of the assessed genes showed significant changes in gene expression in either direction. We then compared the gene expression change in each independent comparison and selected only those genes whose expression significantly increased or decreased in every comparison. The ability to detect important alterations in mRNA levels was increased not only by having three independent comparisons, but also through the elimination of strain background as a variable—the genes identified changed regardless of strain. This led to the identification of 136 genes (1.2%) whose expression consistently increased across every comparison and 78 genes (0.7%) with consistently decreased expression levels. These numbers were significantly greater than the number expected by random chance, 3 and 2 genes, respectively (p<<0.001, chi-square). We reconfirmed the change in gene expression in 16 genes by semi-quantitative RT-PCR and/or northern blots and observed qualitative agreement between the methods for all 16 genes (data not shown).

We were surprised to note that many of the changes in gene expression are the opposite of those previously shown to characterize adipocyte differentiation (Table 1). Several mRNAs that encode proteins involved in lipid metabolism were decreased. These included: ATP-citrate lyase, glycerol 3-P dehydrogenase, stearoyl CoA desaturase and fatty acid binding protein. Adipocyte-specific mRNAs, such as spot14 and adipsin, decreased 4.3- and 8.6-fold respectively. However, leptin mRNA increased, consistent with previous reports in ob/ob mice. Furthermore, genes involved in energy metabolism also showed marked decreases, including aldolase, lactate dehydrogenase and pyruvate carboxylase. Other markers of adipocyte differentiation not directly involved in energy metabolism also showed decreases. For example, the expression of β-3 adrenergic receptor, angiotensinogen, and apolipoprotein E all increase during adipogenesis but showed large decreases in the comparisons of adipose tissue from lean and obese mice.

Another surprising result was the number of genes encoding mitochondrial enzymes whose expression decreased with obesity. Several proteins involved in the electron transport chain, such as cytochrome c1 and cytochrome c oxidase, decreased. The mitochondrial enoyl-CoA hydratase and aldehyde dehydrogenase 2 also showed 2.2- and 2.8-fold decreases, respectively. In contrast, uncoupling protein 2 (UCP2) increased 4-fold in adipose tissue from obese animals.

Large increases in gene expression were observed in genes coding for cytoskeletal and extracellular matrix proteins (Table 2). Expression of type I collagen decreases during adipocyte differentiation but we observed a 2.1-fold increase in the expression of procollagen I. We observed increases in profilin, talin, and actin-binding protein mRNAs consistent with the need to remodel fat pads as adiposity increased. Changes in genes encoding extracellular matrix proteins included increases in the expression levels of cofilin, galactose-binding lectin and the proteoglycan biglycan. Cathepsins are lysosomal proteases also implicated in tissue remodeling. Increases in expression of cathepsins B and D as well as cathepsin K, S, and Z precursors were observed with obesity.

The expression level of certain nuclear proteins and transcription factors was also altered. The gene encoding the Myc basic motif homolog-1 showed a 3.0-fold increase in obese animals. Of particular note, the sterol responsive element binding protein ADD1/SREBP demonstrated a 2.7-fold decrease in expression. SREBP positively regulates many genes coding for lipogenic enzymes and its down-regulation is consistent with the decrease in expression of the lipogenic enzymes mentioned above.

Gene Expression in Obese and Obese-Diabetic Mice. We determined which genes increased or decreased with hyperglycemia across five sets of mice: B6 ob/ob mice, three sets of $F_2$ ob/ob mice with increasing hyperglycemia (mean fasting glucoses of 299, 337, and 410 mg/dl), and BTBR ob/ob mice. By generating an $F_2$ ob/ob population from the parental strains, we created mice with intermediate levels of hyperglycemia ranging from very mild to severe. This allowed us to assess which genes demonstrate a dose-dependent change in gene expression with increasing hyperglycemia. The degree of correlation between the severity of diabetes and gene expression levels was evaluated by linear regression. In white adipose tissue, there were 34 genes (0.3%) whose expression positively correlated (r>0.95) and 58 genes (0.5%) whose expression negatively correlated with diabetes (r<−0.95). As before, we reconfirmed the change in expression for selected genes. The fold change was calculated from the expression levels of the groups with the lowest and highest blood glucose. Many genes that code for signal transduction proteins had expression levels that correlated with the development of diabetes. Genes similar to both Raf and Ras increased with diabetes, as did Fyn. Many signal transduction molecules use SH2 and SH3 domains, and two such proteins, SH3P3 and CISH, decreased with diabetes.

Our analysis also identified several genes encoding proteins involved in protein phosphorylation and dephosphorylation, important mediators of many signaling pathways, including those activated by insulin. In particular, PTPK1, a non-receptor protein tyrosine phosphatase, decreased to undetectable levels as hyperglycemia increased. The expression of Flk-2, a class III receptor tyrosine kinase, increased from undetectable levels with the onset of diabetes. Conversely, CAM-like protein kinase and pim-1 protein kinase decreased significantly with hyperglycemia whereas a phosphatase inhibitor-2-like protein increased with elevated plasma glucose. Expression of vav-T, an SH3 domain containing G-protein exchange factor, decreased 3.3-fold. We also observed that many transcription factor mRNA levels changed with worsening diabetes. BF-2, a winged helix transcription factor, and int-1 increased 2- and 4-fold respectively. Other transcription factors, such as Dlx5, Disheveled (Dvl3), and Pale Ear (ep) decreased with diabetes.

The expression of several genes involved in energy metabolism changed with hyperglycemia. Klbp, a lipid binding protein, increased 7.3-fold while long-chain acyl-CoA dehydrogenase decreased 1.6-fold. AKR1, an aldo-ketoreductase, and fructose-1,6 bis-phosphatase both increased. Interestingly, the b-3 adrenergic receptor decreased 90% in obesity but was positively correlated with increasing plasma glucose. Genetic variations in the the b-3 adrenergic receptor have previously been associated with Type 2 Diabetes Mellitus.

TABLE 1

Genes with decreased expression with obesity in each mouse strain.

| Mouse Gene Accession No. | Description | Fold | Human Homologue Accession No. |
|---|---|---|---|
| Hormones and signal transduction | | | |
| x72862 | β-3-adrenergic receptor | −10.5 | XM_049417 |
| aa500440 | GTP-binding protein ($G_\alpha$i-1) | −2.3 | AF205588 |
| aa529056 | Guanine nucleotide binding protein 11 | −1.6 | XM_004660 |
| u02602 | Thyroid stimulating hormone receptor | −1.5 | XM_007404 |
| X61431 | Diazepam-binding inhibitor | −2 | M14200 |
| AF009246 | Ras-related protein (DEXRAS1) | −2.9 | NM_016084 |

TABLE 1-continued

Genes with decreased expression with obesity in each mouse strain.

| Mouse Gene Accession No. | Description | Fold | Human Homologue Accession No. |
|---|---|---|---|
| Mitochondrial | | | |
| aa245912 | Similar to succinate dehydrogenase | −2 | NM_003000 |
| aa466050 | Similar to cytochrome c1 | −1.8 | BC001006 |
| aa667872 | Similar to ubiquinol-cytochrome c Reductase core protein 2 | −3.4 | NM_003366 |
| aa733351 | Similar to ATP synthase E chain | −2.1 | NM_007100 |
| W42043 | Branched-chain amino acid aminotransferase | −2.8 | U68418 |
| W41817 | Cytochrome c oxidase, subunit VIIIa | −2.7 | XM_006132 |
| U07235 | Aldehyde dehydrogenase (ALDH2) | −3 | XM_007012 |
| D16215 | Flavin-containing monooxygenase | −2.8 | XM_001726 |
| Aa270965 | Mitochondrial enoyl-CoA hydratase | −2.8 | N/a |
| M60798 | SOD-1 | −2.2 | XM_047885 |
| Lipid metabolism | | | |
| D29016 | Squalene synthase | −1.8 | L06105 |
| Aa271471 | ATP citrate-lyase mRNA | −2.9 | XM_036462 |
| D50430 | Glycerol-3-phosphate dehydrogenase | −2.5 | XM_050502 |
| X51905 | Lactate dehydrogenase-B | −3.3 | XM_050074 |
| M21285 | Stearoyl-CoA desaturase | −2.5 | XM_030446 |
| L09192 | Pyruvate carboxylase | −2.1 | NM_022172 |
| Y00516 | Aldolase A | −2.5 | BC010660 |
| AA080172 | Phosphoenolpyruvate carboxykinase | −5.3 | XM_009672 |
| W29562 | 3T3-L1 lipid binding protein | −2.3 | XM_005096 |
| X95279 | Spot14 | −4.6 | Y08409 |
| aa197973 | Similar to biotin carrier protein of methylmalonyl-CoA carobxyl-transferase | −2.4 | XM_037615 |
| Transcription factor | | | |
| AA068578 | add1/SREBP | −2.7 | U00968 |
| Secreted proteins | | | |
| AA106347 | Angiotensinogen precursor | −8.1 | BC011231 |
| W36455 | Adipsin | −8.3 | AJ313463 |
| D00466 | Apolipoprotein E gene | −2.4 | M10065 |
| m60579 | Coplement componenet C2 | −3.2 | XM_004193 |
| Others | | | |
| U63146 | Retinol-binding protein (RBP) | −2.5 | XM_005907 AF119868 NM_006744 X00129 |
| AA049662 | Retinol-binding protein (RBP) | −2.2 | XM_005907 AF119868 NM_006744 X00129 |
| W14367 | Retinol-binding protein (RBP) | −1.8 | XM_005907 AF119868 NM_006744 X00129 |
| AA154594 | Similar to branching enzyme | −2.6 | XM_011011 |
| W85270 | Inorganic pyrophosphatase | −2 | XM_045578 |
| W13498 | Glycogen phosphorylase | −2.5 | N/A |
| AF012431 | D-dopachrome tautomerase (Ddt) | −1.9 | AF058293 |
| L31783 | Uridine kinase | −2.7 | XM_033387 |
| U38940 | Asparagine synthetase | −4 | XM_044503 |
| X51703 | Ubiquitin | −2.7 | XM_037118 |
| aa688469 | Osteogenesis imperfecta (oim) | −3.3 | XM_042194 |
| ab004048 | Neuronatin | −2.8 | XM_009686 |

TABLE 1-continued

Genes with decreased expression with obesity in each mouse strain.

| Mouse Gene Accession No. | Description | Fold | Human Honologue Accession No. |
|---|---|---|---|
| m30844 | B2 protein | −11.2 | AF144686 |
| U19596 | Cdk4 and Cdk6 inhibitor p18 | −2.7 | XM_001304 |
| X14061 | β-globin complex | −2.6 | N/A |
| W82026 | Scr3, ssRNA BP | −2.1 | D28483 |
| W83919 | Elongation factor Tu | −2.3 | XM_017048 |
| M73483 | Glutathione S-transferase | −5.8 | XM_037077 |
| M96827 | Ob/ob haptoglobin | −2.1 | NM_005143 |
| AA059700 | β-2 microglobulin (B2m) | −3.2 | XM_032402 |
| ET61037 | TI-225 | −2.5 | N/A |

TABLE 2

Genes with increased expression with obesity.

| Mouse Gene Accession No. | Description | Fold | Human Homologue Accession No. |
|---|---|---|---|
| Cytoskeleton and ECM | | | |
| X54511 | Myc basic motif homologue-1 | 15 | BC000728 |
| d00472 | Cofilin | 1.7 | XM_053779 |
| m86736 | Acrogranin | 2.7 | XM_045991 |
| u08020 | FVB/N collagen pro-$\alpha$-1 | 2.1 | XM_012651 |
| u27340 | Sulfated glycoprotein (Sgp 1) | 3.1 | XM_045137 |
| x56123 | Talin | 7.7 | XM_005392 |
| W10936 | L-34 galactoside-binding lectin | 4.5 | NM_002306 |
| AA003323 | Similar to filamin A | 4.5 | NM_001456 |
| X99347 | LPS-binding protein | 1.9 | XM_012965 |
| X14425 | Profilin | 2.1 | XM_028379 |
| X75285 | Fibulin-2. | 2.2 | XM_051629 |
| L20276 | Biglycan (Bgn) | 2.1 | BC004244 |
| D13664 | Osteoblast specific factor 2 (OSF-2) | 3.1 | NM_006475 |
| Lysosomal | | | |
| aa255186 | Similar to cathespin S precursor | 5.6 | XM_041904 |
| X94444 | Preprocathepsin K. | 4.5 | XM_041899 |
| AA106931 | γ-IFN inducible lysosomal thiol reductase (GILT) | 6 | XM-038147 |
| M65270 | Cathepsin B | 3.5 | N/A |
| AA116604 | Cathepsin Z precursor (Ctsz) | 3.9 | XM_030701 |
| AA107895 | Cathepsin D | 2.1 | XM_006121 |
| AA146437 | Cathepsin S precursor | 7.7 | XM_041904 |
| ab009287 | Macrosialin | 6.6 | AC007421 |
| AA000961 | Preprolegumain | 3.9 | D55696 |
| AA117064 | Vacuolar adenosine triphosphatase | 1.9 | XM_005227 |
| Immune/complement genes | | | |
| aa711625 | Similar IFN-$\alpha$ induced protein | 2.8 | XM_016486 |
| ET62967 | Complement C1q precursor | 1.4 | N/A |
| m22531 | Complement C1q β chain | 2.6 | XM_010666 |
| J05020 | High affinity IgE receptor | 2.5 | XM_042451 |
| m14215 | Fc γ receptor | 4.8 | X17652 |
| W41745 | Fc receptor (Fcer1γ) | 8.1 | XM_042451 |
| L39357 | Migration inhibitory factor (Mif) | 1.6 | L19686 |
| u19482 | C10-like chemokine | 3.3 | N/A |
| Z11974 | Macrophage mannose receptor | 3.7 | XM_005830 |
| X67469 | AM2 receptor | 1.7 | NM_002332 |
| L20315 | MPS1 | 5.4 | L20314 |
| X91144 | P-selectin glycoprotein ligand | 2.8 | XM_006867 |
| Z16078 | CD53 gene exon 7 | 2.2 | L11670 |

TABLE 2-continued

Genes with increased expression with obesity.

| Mouse Gene Accession No. | Description | Fold | Human Homologue Accession No. |
|---|---|---|---|
| Cytoskeleton and ECM | | | |
| W11011 | Nedd8 | 1.4 | XM_017573 |
| W08269 | Pigment epithelium-derived factor | 2.3 | AF400442 |
| AA097711 | Tropomyosin (TM-4) | 2.2 | BC002827 |
| U72680 | Ion channel homolog RIC | 3 | XM_015774 |
| AA096813 | Cysteine proteinase | 2.2 | AC009123 |
| M73741 | α-B2-crystallin gene | 2.8 | M28638 |
| W15873 | Similar to Tctex1 | 1.5 | D50663 |
| Cell proliferation | | | |
| U44426 | D52 (mD52) | 5.2 | XM_005272 |
| X06368 | c-fms proto-oncogene | 2.5 | XM_003789 |
| J05261 | Mouse protective protein (Mo54) | 2.6 | XM_009489 |
| AA050703 | Defender against cell death 1 | 1.7 | XM-033470 |
| Adipose-specific genes | | | |
| M93275 | ADRP | 4.2 | XM-048266 |
| U18812 | Leptin | 3 | XM_045426 |
| Membrane proteins | | | |
| W64897 | Phosphatidylinositol transfer protein | 1.8 | NM_006224 |
| u37226 | Phospholipid transfer protein | 3.4 | XM_009490 |
| AA031158 | Brain acid-soluble protein 1 | 4.5 | NM_0006317 |
| AA108956 | Similar to human membrane protein | 1.8 | L09260 |
| AF026124 | Schwannoma-associated protein | 3.9 | XM_047409 |
| AA108330 | Astrocytic phosphoprotein | 1.9 | XM_001279 |
| Others | | | |
| u69135 | UCP2 | 4.3 | BC011737 |
| u29539 | Retinoic acid-inducible E3 protein | 3.4 | U30498 |
| U59807 | Cystatin B (Stfb) | 4.4 | AC079869 |
| K02236 | Metallothionein II (MT-II) | 2.6 | J00271 |
| M38337 | Milk fat globule membrane protein E8 | 3.1 | XM_031292 |
| M73706 | Ferritin large subunit | 1.9 | XM_050469 |
| W75072 | Creatine kinase B | 3.4 | N/A |
| W83564 | 5-lipoxygenase-activating protein | 3.4 | XM_015396 |
| AA106783 | Poly A binding protein | 1.8 | XM_042055 |
| x84797 | Similar to human hematopoietic specific protein 1 | 4 | NM_005335 |
| X61970 | Growth factor-inducible immediate early gene (3CH134) | 2.6 | XM_003720 |

TABLE 3

Genes correlated with the development of hyperglycemia.

| Mouse Gene Accession No. | Description | r value | Fold | Human Homologue Accession No. |
|---|---|---|---|---|
| Signal transduction | | | | |
| M34397 | IL-3 receptor-like protein | −0.955 | −3.5 | XM_009960 |
| aa097386 | Similar to CAM-like protein kinase | −0.982 | n/a | XM_002911 |
| U58889 | SH3-containing protein (SH3P3) | −0.970 | n/a | XM_005175 |
| u35124 | Nonreceptor tyrosine phosphatase | −0.968 | n/a | XM_002447 |
| d31943 | Cytokine inducible SH2-containing protein | −0.971 | −2.2 | XM_002835 |
| u60528 | Guanylin precursor gene | 0.963 | n/a | N/A |
| aa217487 | Similar to mouse pim-1 protein kinase | −0.972 | n/a | M16750 |
| m64689 | flk-2 | 0.972 | n/a | XM_039994 |
| C79373 | Similar to phosphatase inhibitor-2 | 0.952 | 1.5 | XM_049288 |
| aa105135 | Similar to P53-binding protein | −0.982 | −2.4 | XM_032359 |
| aa467011 | Similar to LMW G-protein | 0.955 | n/a | XM_031430 |
| d83266 | vav-T | −0.958 | n/a | XM_044621 |
| W91283 | Similar to human ras-like protein | 0.989 | 1.6 | M31468 |
| C81377 | Similar to rat activated c-raf oncogene | 0.960 | n/a | XM_051580 |
| u70324 | Fyn(T) | 0.965 | n/a | XM_040354 |
| X72862 | β-3-adrenergic receptor | 0.951 | n/a | XM_049417 |
| L01695 | Calmodulin-dependent phosphodiesterase | −0.960 | −1.2 | XM_006812 |
| x04648 | IgG1/IgG2β Fc receptor (FcR) | −0.961 | −3.3 | X17652 |

TABLE 3-continued

Genes correlated with the development of hyperglycemia.

| Mouse Gene Accession No. | Description | r value | Fold | Human Homologue Accession No. |
|---|---|---|---|---|
| Secreted proteins | | | | |
| M33960 | Plasminogen activator inhibitor (PAI-1) | 0.962 | 2.2 | XM_051248 |
| D38580 | VNSP 1 (vomeronasal secretory protein I) | −0.962 | n/a | XM_009475 |
| Protein synthesis and processing | | | | |
| aa036204 | Similar to human 40S ribosomal protein S24 | 0.971 | 1.7 | XM_051716 |
| D12907 | 47-kDa heat shock protein (HSP47) | −0.966 | −1.6 | NM_004353 |
| L25913 | Chaperonin | 0.999 | 1.5 | AF026291 |
| C77806 | Similar to rat carboxypeptidase B gene | −0.960 | n/a | AF144685 |
| aa270493 | Similar to deoxyhypusine synthase | −0.959 | −2.4 | XM_032647 |
| aa611449 | Similar to Homo sapiens HSPC183 | −0.962 | −2.6 | AF151017 |
| AA105758 | MDj10 | −0.974 | −2.2 | XM_032485 |
| Cytoskeletal and ECM | | | | |
| M25825 | tctex-1 | −0.959 | −1.9 | D50663 |
| C77864 | Similar to Chinese hamster for β tubulin | −0.991 | n/a | BC012835 |
| aa111610 | Similar to tuftelin-interacting protein 10 | 0.950 | n/a | BC013051 |
| AA138226 | Similar to rat clathrin light chain (LCB3) | 0.956 | 1.1 | BC006457 |
| m75720 | α-1 protease inhibitor 3 | 0.955 | n/a | XM_028358 |
| C76274 | Similar to Mus musculus ligatin (Lgtn) | −0.955 | n/a | XM_051973 |
| aa204573 | Similar to human spindle pole body protein | −0.972 | −1.5 | XM_027551 |
| Transcription factors | | | | |
| W87135 | Single stranded DNA binding protein p9 | 0.973 | 2.2 | X79805 |
| af003866 | Pale ear (ep wild type allele) | −0.982 | −2.1 | XM_050813 |
| AB001990 | Dcra | −0.985 | −1.4 | NM_006052 |
| m11943 | Int-1 proto-oncogene | 0.956 | 4 | XM_006776 |
| u67840 | D1x5 | −0.988 | n/a | XM_004848 |
| Z32675 | Hairless protein | −0.956 | −1.9 | NM_018411 |
| AJ002366 | Transcription factor TFIIH, 62 kD subunit | −0.968 | n/a | BC000365 |
| U41285 | Dishevelled-3 (Dvl-3) | −0.951 | −1.5 | XM_029104 |
| L38607 | BF-2 transcription factor | 0.944 | n/a | XM_003984 |
| aa710439 | BACH1 | −0.986 | n/a | XM_009718 |
| W83286 | Similar to H. sapiens RNA polymerase II | 0.967 | 1.4 | NM_006232 |
| D14336 | RNA polymerase I associated factor | −0.972 | −1.5 | AK024032 |
| Others | | | | |
| aa711217 | Similar to NADH-ubiquinone oxidoreductase | 0.960 | 1.4 | AF035839 |
| aa521794 | Similar to cytochrome c oxidase | −0.961 | −1.6 | XM_041174 |
| M36660 | NAD(P) H menadione oxidoreductase | −0.958 | n/a | J03934 |
| af015284 | Selenoprotein W (mSelW) | −0.992 | n/a | U67171 |
| M99054 | Acid phosphatase type 5 gene | −0.960 | −1.5 | X67123 |
| aa543785 | Thymic dendritic cell-derived factor 1 | 0.985 | 1.5 | XM_038905 |
| J02809 | Neural specific calmodulin-binding protein | −0.954 | n/a | XM_045289 |
| aa061099 | Ribonuclease HI | −0.980 | −3.3 | NM_006397 |
| C78741 | Poly(A) binding protein II (mPABII) | −0.951 | −1.4 | AF026029 |
| AA230943 | Similar to mouse Sm-B | −0.952 | −2.1 | XM_044910 |
| aa544831 | Similar to renin-binding protein | −0.973 | −2.5 | XM_013053 |
| U12564 | 129 defensin-like gene 4C-2 | 0.971 | n/a | N/A |
| c79315 | Similar to M. musculus tex 292 | 0.971 | 1.6 | XM_039300 |

TABLE 3-continued

Genes correlated with the development of hyperglycemia.

| Mouse Gene Accession No. | Description | r value | Fold | Human Homologue Accession No. |
|---|---|---|---|---|
| L06234 | Dihydropyridine-sensitive calcium channel | −0.969 | n/a | XM_001910 |
| U62021 | Neuronal pentraxin 1 (NPTX1) | −0.951 | −2.1 | NM_002522 |
| aa560507 | Similar to antiquitin | −0.984 | −1.6 | BC002515 |
| z72000 | BTG3 | 0.959 | 2.1 | XM_012976 |
| af003346 | Ubiquitin-conjugating enzyme UbcM2 | 0.982 | 1.7 | AF085362 |
| AA072822 | Testosterone 15-$\alpha$-hydroxylase | −0.957 | n/a | XM_030948 |
| aa547057 | Similar to HT Protein | −0.979 | −1.4 | BC002894 |
| Metabolism | | | | |
| AA146156 | Keratinocyte lipid binding protein (Klbp) | 0.986 | 8.6 | XM_015760 |
| AA120674 | Similar to *Homo sapiens* acylephosphatase 2 | 0.964 | 2.3 | NM_001108 BC012290 |
| U21489 | Long-chain acyl-CoA dehydrogenase | −0.963 | −1.6 | XM_002386 |
| aa592828 | Aldo-keto reductase AKR1C1 | 0.977 | 2.2 | N/A |
| ET63206 | Fructose-1,6-biphosphatase | 0.960 | n/a | N/A |

We claim:

1. A method of diagnosing susceptibility to obesity in a human comprising the steps of
   determining the expression pattern of a gene encoding add1/SREBP in the adipose tissue of the human;
   comparing the expression pattern of the gene encoding add1/SREBP of the human with that of a non-obese human; and
   diagnosing the human as susceptible to obesity if the expression of the gene encoding add1/SREBP is decreased as compared to that of the non-obese human.

2. A method of diagnosing susceptibility to obesity in a human comprising the steps of
   determining the expression pattern of a gene encoding add1/SREBP in combination with a gene encoding cytochrome c oxidase subunit VIIa and a gene encoding stearoyl-CoA desaturase in the adipose tissue of the human;
   comparing the expression pattern of the gene encoding add1/SREBP in combination with the gene encoding cytochrome c oxidase subunit VIIa and the gene encoding stearoyl-CoA desaturase from the human with that of a non-obese human; and
   diagnosing the human as susceptible to obesity if the expression of said genes is decreased as compared to the non-obese human.

3. A method of diagnosing susceptibility to obesity in a human comprising the steps of
   determining the expression pattern of a gene encoding add1/SREBP in combination with a gene encoding cytochrome c oxidase subunit VIIa in the adipose tissue of the human;
   comparing the expression pattern of the gene encoding add1/SREBP in combination with the gene encoding cytochrome c oxidase subunit VIIa from the human with that of a non-obese human; and
   diagnosing the human as susceptible to obesity if the expression of said genes is decreased as compared to the non-obese human.

4. A method of diagnosing susceptibility to obesity in a human comprising the steps of
   determining the expression pattern of a gene encoding add1/SREBP in combination with a gene encoding stearoyl-CoA desaturase in the adipose tissue of the human;
   comparing the expression pattern of the gene encoding add1/SREBP in combination with the gene encoding stearoyl-CoA desaturase from the human with that of a non-obese human; and
   diagnosing the human as susceptible to obesity if the expression of said genes is decreased as compared to the non-obese human.

5. A method of assessing susceptibility to obesity in a human, the method comprising the steps of:
   determining the expression pattern of a gene encoding add1/SREBP, in the adipose tissue of the human; and
   comparing the expression pattern of the gene encoding add1/SREBP in of the human with that of a non-obese human, wherein a decrease in the expression of the gene encoding add1/SREBP in the human as compared to the non-obese human is indicative of susceptibility to obesity in the human.

* * * * *